(12) United States Patent
Black et al.

(10) Patent No.: US 6,245,083 B1
(45) Date of Patent: Jun. 12, 2001

(54) SUTURELESS ANASTOMOTIC TECHNIQUE USING A BIOADHESIVE AND DEVICE THEREFOR

(75) Inventors: Kirby S. Black, Acworth, GA (US); Steve Gundry, Redhands, CA (US); Ümit Yüksel, Kennesaw, GA (US)

(73) Assignee: Cryolife, Inc., Kennesaw, GA (US)

( * ) Notice: Subject to any disclaimer, the term of this patent is extended or adjusted under 35 U.S.C. 154(b) by 0 days.

(21) Appl. No.: 09/443,588

(22) Filed: Nov. 19, 1999

Related U.S. Application Data (63) Continuation of application No. 09/161,101, filed on Sep. 25, 1998.

(51) Int. Cl.$^7$ .................................................. A61B 17/00
(52) U.S. Cl. .......................................................... 606/153
(58) Field of Search ................................... 606/213, 159, 606/151, 153, 152, 155, 108; 604/22, 27, 28

(56) References Cited

U.S. PATENT DOCUMENTS 5,395,311 * 3/1995 Andrews ................................ 604/22

* cited by examiner

*Primary Examiner*—Olik Chaudhuri
*Assistant Examiner*—Hoa B. Trinh
(74) *Attorney, Agent, or Firm*—Kenyon & Kenyon (57) ABSTRACT

A method of anastomosing two hollow bodily organs using a bioadhesive. The method involves apposing apertures in the organs to be joined and applying the bioadhesive, thereby joining the apertures in the organs and allowing movement of fluid or semi-solid material from one of the two organs to the second organ. The invention also relates to a device for anastomosing two hollow organs. The device has two inflatable balloons, one of which is placed into the lumen each of the two organs to be joined. Inflation of the balloons holds the apertures together while the bioadhesive is applied. The device allows anastomosis of blood vessels through endoscopic means.

34 Claims, 5 Drawing Sheets

SUTURELESS ANASTOMOTIC TECHNIQUE USING A BIOADHESIVE AND DEVICE THEREFOR

This application is a continuation of U.S. Ser. No. 09/161,101, filed Sep. 25, 1998, now pending.

BACKGROUND OF THE INVENTION

As part of the treatment for trauma and many types of disease processes it is often necessary to join blood vessels to re-establish blood flow to some portion of the body or to an organ. Such joinder of blood vessels is referred to as vascular anastomosis. In the past, the primary method of closing vascular anastomosis sites has been manual suturing; this continues to be the method of choice for vascular anastomosis in most surgical subspecialties and procedures. In the majority of surgical procedures there is adequate time and the surgical site is suitable for manual suturing to be used for vascular anastomosis. For example, in most cardiac bypass surgeries, the surgical approach and anesthetic regimen traditionally employed have allowed the access and site stability necessary for manual suturing of any required vascular anastomosis.

Traditional coronary bypass surgery involves splitting and retracting the patient's sternum and opening the thoracic cavity. The invasive nature of the standard cardiac bypass surgical approach carries with it a significant cost in morbidity and mortality. Less invasive surgical methods would offer faster healing times with potentially less pain and fewer post-surgical complications.

Recently, cardiac bypass surgery has been moving toward less invasive surgical approaches. Although some endoscopic cardiac surgeries have been described, endoscopic cardiac bypass surgery has not been possible. Endoscopic cardiac bypass surgery raises at least two major technical problems related to vascular anastomosis: 1) the surgical exposure and surgical manipulation do not allow for manual suturing; and 2) anastomosis of the vessels adjacent to the beating heart must occur while the vessels are moving. Thus, the ability to anastomose vessels during endoscopic cardiac bypass surgery would provide a method of joining the vessels without the use of manual sutures while at least one of the vessels is in motion. No vascular anastomosis techniques currently in practice are suitable for performing vascular anastomosis through a small surgical window, such as those created for a laparoscope, or via endoscopy and under circumstances wherein at least one of the vessels is in motion or an organ in the surgical field is in motion.

Even without the restrictions imposed by a limited surgical exposure and a moving blood vessel, manual suturing has another problematic characteristic: it is time consuming. There has, therefore, always been incentive to find a method of vascular anastomosis that provides the strength and reliability of manual suturing but which can be performed more rapidly. Faster anastomotic techniques would lead to shorter surgical times, thereby decreasing patient morbidity and mortality stemming from surgical procedures, especially extended procedures. The present invention also addresses this problem by providing a rapid method of performing vascular anastomosis.

SUMMARY OF THE INVENTION

This invention is directed to a method of joining one or more hollow bodily organs by juxtaposing apertures in those organs in apposition and applying an amount of bioadhesive sufficient to join the organs in a manner which enables movement of blood or other material between the organs. The bioadhesive used in the invention is cross-linked proteinaceous material which is non-toxic and sets rapidly. The method is applicable to join organs in side-to-side, end-to-side or end-to-end fashion and is preferably used with blood vessels, lymphatic vessels or organs of the intestinal tract. The method is particularly useful in surgeries wherein one of the organs is moving, e.g., when surgery is performed on the artery of a beating heart.

In a further embodiment of the invention, when the method is used to join two blood vessels in side-to-side fashion, the method further comprises extending a guide wire from one vessel lumen through the apertures into the lumen of the second vessel, feeding a dual balloon catheter along the guide wire to position a balloon within the lumen of each vessel and expanding the balloons to stabilize the vessels and hold the apertures in apposition. This method is preferred for joining the internal thoracic artery to a branch of the left coronary artery while performing endoscopic cardiac bypass surgery in the presence of a beating heart.

The invention also relates to a dual balloon catheter for holding apertures in two hollow bodily organs in apposition for application of bioadhesive. Specifically the invention relates to a device having a first flexible, elongated structure with a first longitudinal lumen and proximal and distal annular inflatable balloons. The distal annular inflatable balloon is provided around a distal portion of the first elongated structure so that, in an operative position, the distal annular inflatable balloon is located within the lumen of one of the hollow bodily organs to be joined. The proximal annular inflatable balloon is provided around the first elongated structure and proximal to the distal balloon. The device may also include a separate additional longitudinal lumen in the first elongated structure for inflating the proximal and distal balloons with fluid or air. Alternatively, the first elongated structure has two additional longitudinal lumina, one lumen for each of the proximal and distal balloons. The device also optionally provides a second flexible, elongated structure, which resides within and is slidably received within the first longitudinal lumen. The distal end of the second elongated structure includes a tissue piercing tip, or alternatively, a needle. The second elongated structure optionally contains a longitudinal lumen extending from the proximal end of the second elongated structure to the distal end of the tissue piercing tip.

The second elongated structure is selectively extendable distally past the distal end of the first elongated structure and optionally locked into an extended position, thus allowing the piercing tip to be used to pierce the walls of the organs to be joined. The second elongated structure has a second, retracted, position, in which it may be locked. In the retracted position, the tissue piercing tip is retracted within the first elongated structure where it cannot damage the organ tissues.

The device may also optionally include a guide wire slidably received within the second longitudinal lumen. The guide wire is extendable into two positions: a guiding position, in which the distal end of the guide wire is extended distally beyond the distal end of the piercing tip of the second elongated structure; and a non-guiding position, in which the distal end of the guide wire is retracted inside the piercing tip.

In another embodiment the proximal and distal balloons can slide in relation to one another such that the balloons can be moved closer or further apart. In this embodiment, the device comprises a first flexible elongated structure with a proximal annular inflatable balloon disposed around the distal portion of the first elongated structure. The first elongated structure also has a longitudinal lumen extending within the first elongated structure. The device further comprises a second flexible elongated structure slidably received within the first longitudinal lumen, the second elongated structure having a distal annular inflatable balloon provided around the distal portion of the second elongated structure. When the device is in an operative position, the distal balloon is received within the second organ and the proximal balloon is received within the first organ. The device according to this embodiment thus has two positions in relation to the proximal and distal balloon: an apposed position, in which the proximal inflatable balloon and the distal inflatable balloon are close together; and an non-apposed position, wherein the distance between the proximal inflatable balloon and the distal inflatable balloon is larger than in the apposed position.

The device according to this embodiment also optionally includes a second longitudinal lumen extending within the second elongated structure and a third flexible elongated structure, slidably received within the second longitudinal lumen. The distal end of the third elongated structure forms a tissue piercing tip, and the device has two positions into which the device may optionally be locked: a piercing position, in which the tissue piercing tip extends distally beyond the distal end of the second elongated structure; and a retracted position, wherein the tissue piercing tip is retracted within the second elongated structure.

The device may also optionally include a third longitudinal lumen extending within the third elongated structure and a guide wire slidably received within the third longitudinal lumen. The guide wire extends into two positions: a guiding position, in which the distal end of the guide wire is extended distally beyond the distal end of the piercing tip; and a non-guiding position, in which the distal end of the guide wire is retracted inside the piercing tip of the third elongated structure.

The alternative embodiment may also optionally include a longitudinal lumen extending within the first elongated structure from the proximal inflatable balloon to the proximal end of the first elongated structure, and a longitudinal lumen extending within the second elongated structure from the distal inflatable balloon to the second proximal end of the second elongated structure.

DETAILED DESCRIPTION OF THE INVENTION

Figures 1, 2, 3:
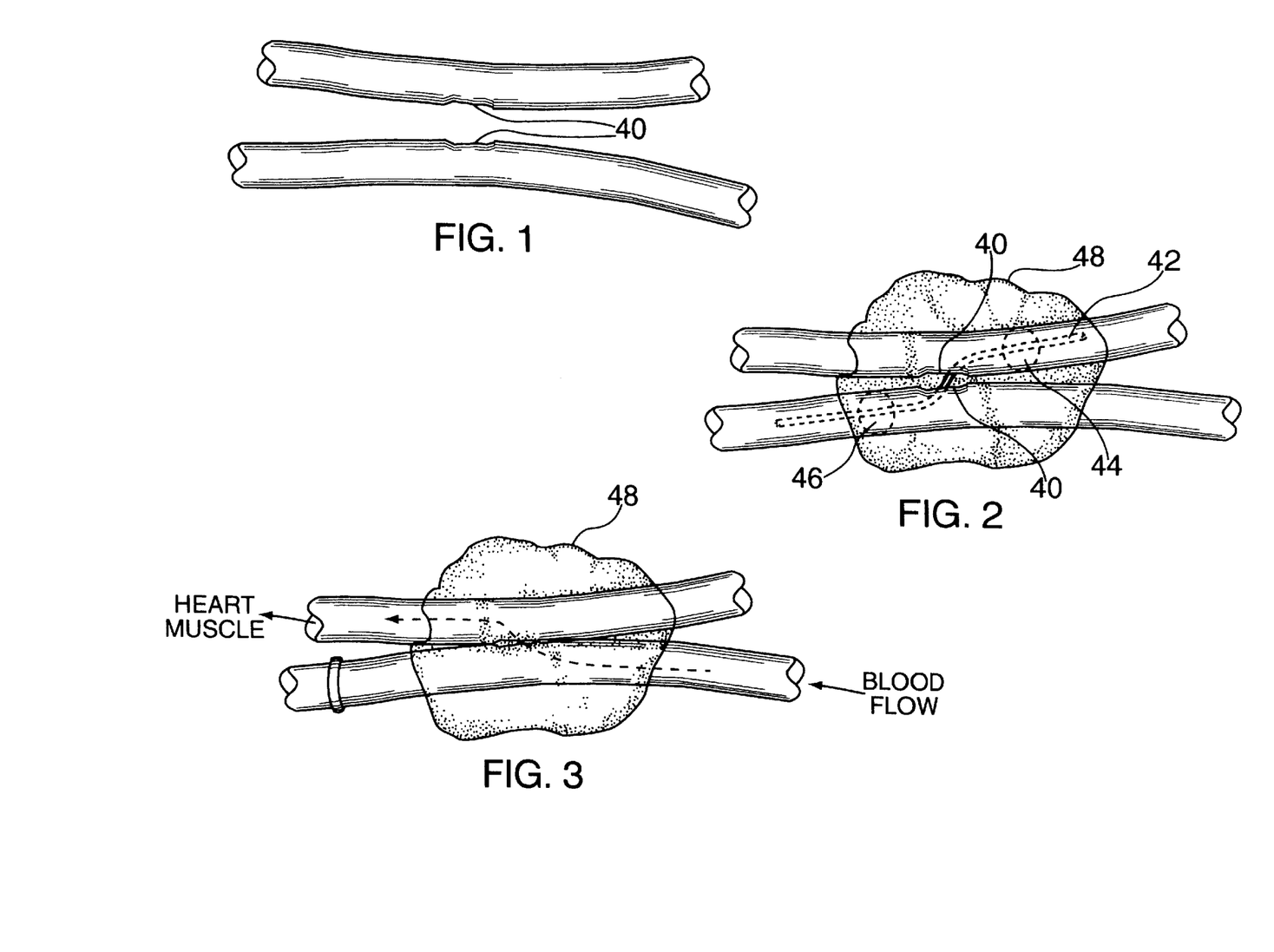
FIG. 1 illustrates two tubular organs with apposed arteriotomy sites 40.
FIG. 2 illustrates a dual balloon catheter device 42 threaded through the arteriotomy sites 40 of FIG. 1, inflated balloons 44 and 46 to hold the organs together and the general location of the bioadhesive 48 relative thereto.
FIG. 3. illustrates a representative vascular anastomosis site after joining a blocked coronary artery to another blood vessel in accordance with the methods of the invention.

The invention provides a method of joining organs, at least one of which has an internal cavity, using a bioadhesive comprised of cross-linked proteinaceous materials. In detail, the invention provides a method for joining hollow bodily organs wherein apertures in the organs are held in apposition and the organs are joined together using the bioadhesive of the invention. The amount of bioadhesive used is sufficient to seal the joined organs so that the apertures communicate, thereby enabling materials to move from one organ to the other through the apertures, as shown, for example, in FIGS. 1 through 3.

As used herein, "hollow bodily organs" and "organs" are used interchangeably and include, without limitation, veins, arteries, lymphatic vessels, esophagus, stomach, duodenum, jejunum, ileum, colon, rectum, urinary bladder, ureters, gall bladder, bile ducts, pancreatic duct, pericardial sac, peritoneum, and pleura. Preferably, the bodily organs to be joined are veins, arteries and portions of the intestinal tract. Most preferably, the organs to be joined are arteries.

Apertures can be created in the organs to be joined by cutting the wall of the organ using a scalpel, radiosurgery unit, laser, trocar, needle or other means. The apertures can also be created using a device having a retractable needle. These apertures are large enough such that the instrument used to hold the apertures in apposition may be introduced into the organ cavity. The size of the aperture can be determined by the function the anastomosis is intended to serve and the materials intended to be moving through the anastomosis site (e.g., fluid versus semi-fluid material such as bowel contents). Alternatively, the apertures can already be present in the organs, such as the end of a tubular organ, or have been created by trauma.

The apertures in the organs can be held in apposition manually or through the use of a device introduced into each organ. The device can aid in positioning the apertures such that they are directly opposite one another. When the apertures are held together, an anastomosis site is formed at the interface of the two organs to which the bioadhesive of the present invention is applied. For example, a device can be attached to each organ through the use of expandable balloons that become stabilized within the organs when they are inflated. The expandable balloons can be attached to one another by a means extending through the apertures. Hence, for example, the device according to the invention can dilate an arteriotomy site and hold the vessels to be anastomosed in contact while the gluing procedure is performed.

The apertures are generally maintained in apposition during application and setting of the bioadhesive. Once the bioadhesive sets, the cavities of the two organs can communicate through the joined apertures. Communication between the two organs means that body fluids or other materials can flow from one organ to another in the manner typically associated with the organ pair that has is been joined. Examples of materials that might flow through an anastomosis include, but are not limited to, liquid and semi-solid materials such as blood, urine, lymphatic fluid, bile, pancreatic fluid, ingesta and purulent discharge.

The bioadhesive of the invention is a non-toxic adhesive having the capability to adhere to biological tissues, reach stability quickly (typically within about 30 seconds to about 5 minutes), preferably set in wet conditions, bond to both biological tissues and synthetic materials, and provide sufficient strength to stabilize the anastomosis. Bioadhesive compositions made up of proteinaceous material and a cross-linking agent have these characteristics. Bioadhesive compositions containing protein and a cross-linking agent are disclosed by U.S. Pat. No. 5,385,606, which is hereby incorporated herein by reference, and are the preferred bioadhesives for use in the method of the invention.

The bioadhesive compositions disclosed by U.S. Pat. No. 5,385,606 contain two components: 1) from 27–53% by weight proteinaceous material; and 2) di- or polyaldehydes in a weight ratio of one part by weight to every 20–60 parts of protein present. The two parts are mixed and allowed to react on the surface to be bonded. Bond formation is rapid, generally requiring less than one minute to complete. The resulting adhesion is strong, generally providing bonds with tear strengths of 400–600 g/cm$^2$. Tear strengths of 1300 g/cm$^2$ have been obtained.

The bioadhesive is applied by extruding the two component solutions through an extruding device having a mixing tip. The bioadhesive is extruded onto the interface of the two organs, the bioadhesive enveloping the anastomosis site sufficiently to hold together the two anastomosed organs, and the communicating apertures. During flexible or rigid endoscopic anastomosis, the bioadhesive may be applied by an applicator directed through the endoscope or by an applicator introduced into the surgical field via a different opening.

It is noted that the method of this invention is amenable to use not only in all areas of vascular surgery but also in other surgical procedures for joining organs. Examples of anastomoses that can be performed include, but are not limited to, arterial anastomosis, venous anastomosis, anastomosis of lymphatic vessels, gastroesophageal anastomosis, gastroduodenal anastomosis, gastrojejunal anastomosis, anastomosis between and among the jejunum, ileum, colon and rectum, ureterovesicular anastomosis, anastomosis of the gall bladder or bile duct to the duodenum, and anastomosis of the pancreatic duct to the duodenum. Preferably, the method is used for vascular anastomoses and gastrointestinal anastomoses. More preferably, the method is used for arterial anastomoses.

More particularly, the invention relates to a method of joining, or anastomosing, tubular organs in a side-to-side or end-to-side fashion using bioadhesive.

The details of the invention can be exemplified in terms of performing coronary bypass surgery. For example, anastomosis of the internal mammary artery (hereinafter "IMA"), also called the internal thoracic artery, to a branch of the left coronary artery to provide blood flow to the left coronary artery can be performed as follows.

The IMA is isolated from the chest wall and is clamped at a location proximal to the intended site of anastomosis. The IMA is completely incised at a location distal to the intended site of anastomosis and the artery is elevated for the remainder of the procedure. An aperture, or arteriotomy, is produced in the IMA by making an incision in the arterial wall. The artery to which the IMA is to be anastomosed, the host artery, is then isolated and an arteriotomy is produced at the appropriate site. In the case of coronary bypass surgery, the host artery is often a branch of the left coronary artery, typically, the anterior descending (interventricular) ramus of the left coronary artery (hereinafter "LAD").

A device is used to stabilize the arteriotomies in apposition to one another. For example, a dual balloon catheter can be used to stabilize the arteriotomies. The dual balloon catheter is introduced into the IMA through the incised distal end and is threaded proximally in the IMA toward the arteriotomy site. The catheter is then threaded through the IMA arteriotomy and into the LAD arteriotomy. The catheter is then threaded an appropriate distance proximally in the LAD such that one balloon of the dual balloon catheter is located within the IMA (the proximal balloon) and the second balloon is located within the LAD (the distal balloon).

The distal balloon is inflated to a pressure sufficient to stabilize the balloon within the LAD.

After the distal balloon is inflated and stabilized, the IMA is positioned alongside the LAD such that the arteriotomy sites are directly apposed. The proximal balloon is then inflated such that the proximal balloon is stabilized within the IMA. This arrangement permits the arteriotomies to be held in apposition despite the movement of the beating heart.

Bioadhesive is then applied around the apposed arteriotomy sites in an amount sufficient to seal the anastomosis site. The catheter is maintained within the anastomosis site with the balloons inflated until the bioadhesive reaches sufficient strength to maintain the integrity of the anastomosis site.

After the adhesive reaches the proper strength, the balloons of the dual balloon catheter are deflated and the catheter is removed. The distal end of the IMA can be ligated using sutures, staples or clips and the proximal clamp is removed from the IMA. Blood flow is thereby established from the IMA, through the anastomosis site, into the LAD.

Figure 4A:
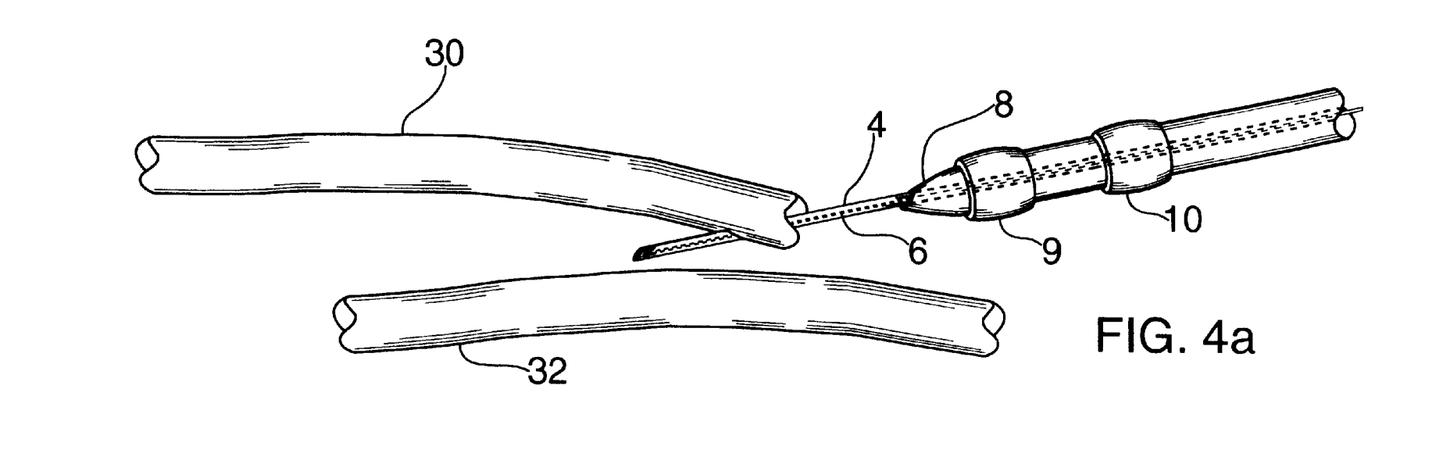
FIG. 4. provides an illustrative example of steps to create a vascular anastomosis between the IMA and the LAD in accordance with the invention.
Figure 4B:
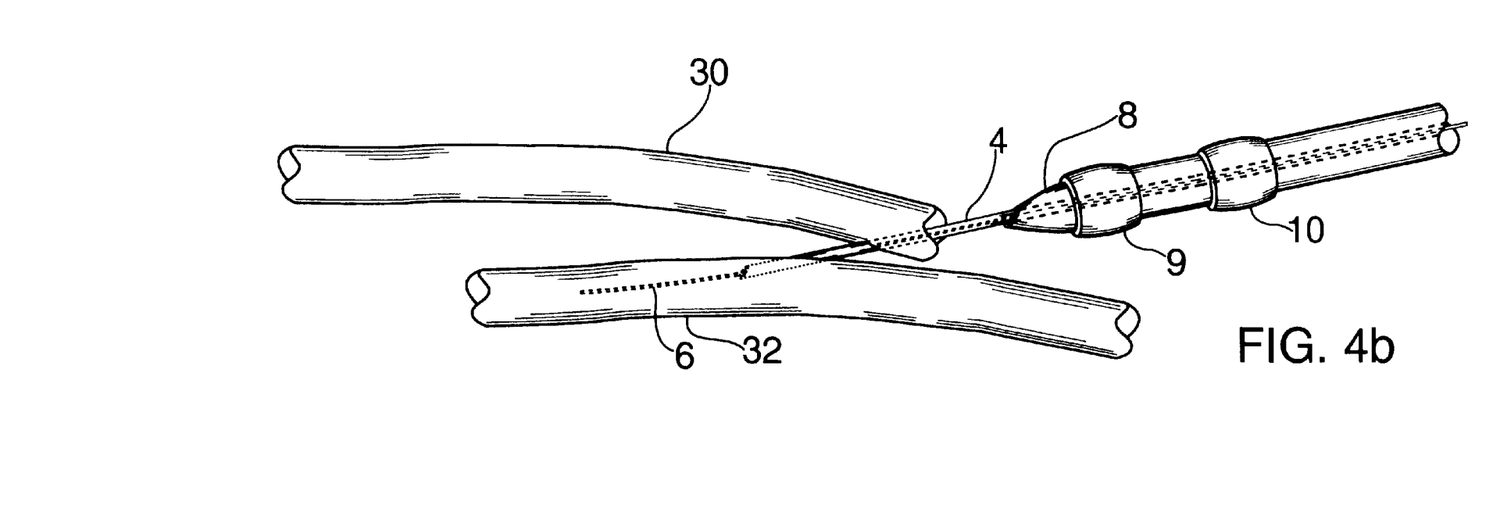
Figure 4C:
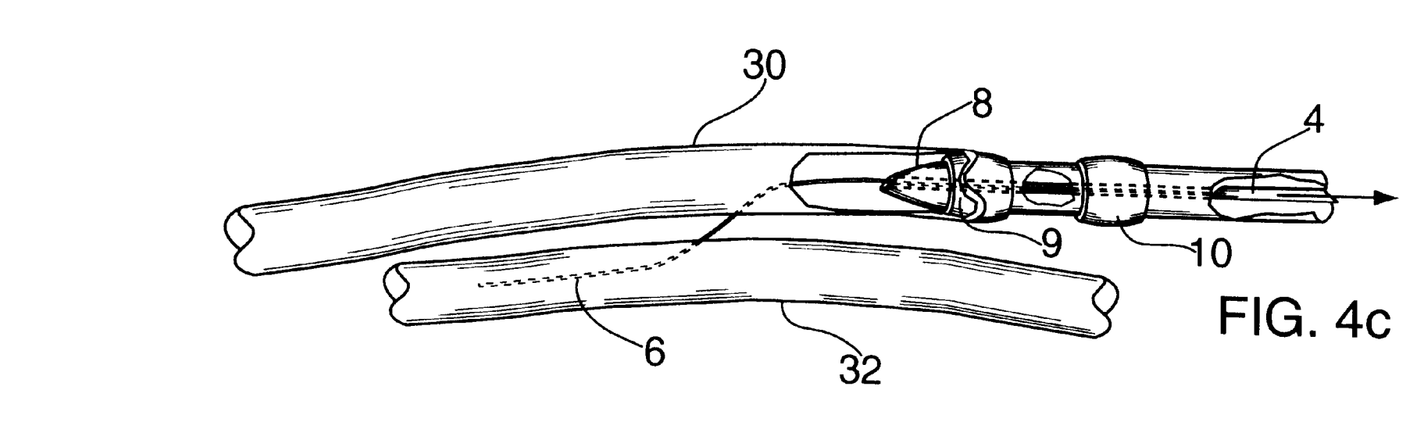
Figure 4D:
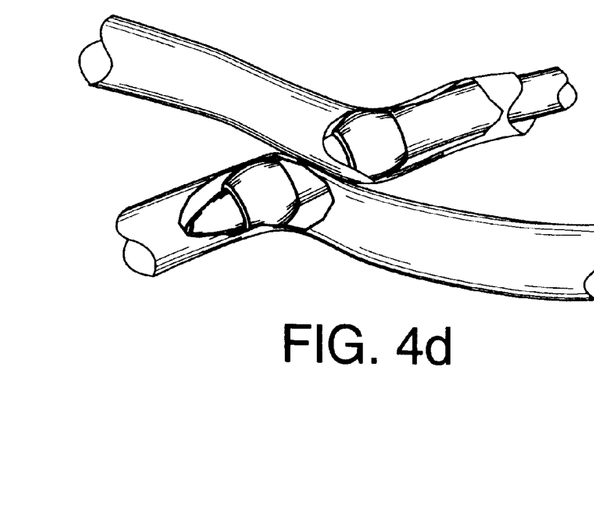
Figure 4E:
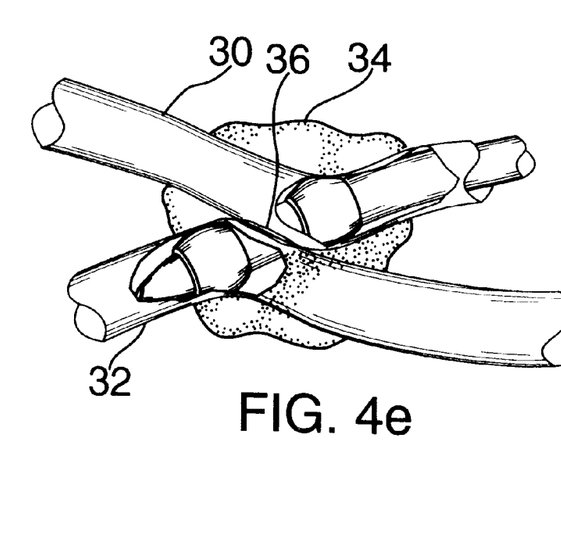
Figure 4F:
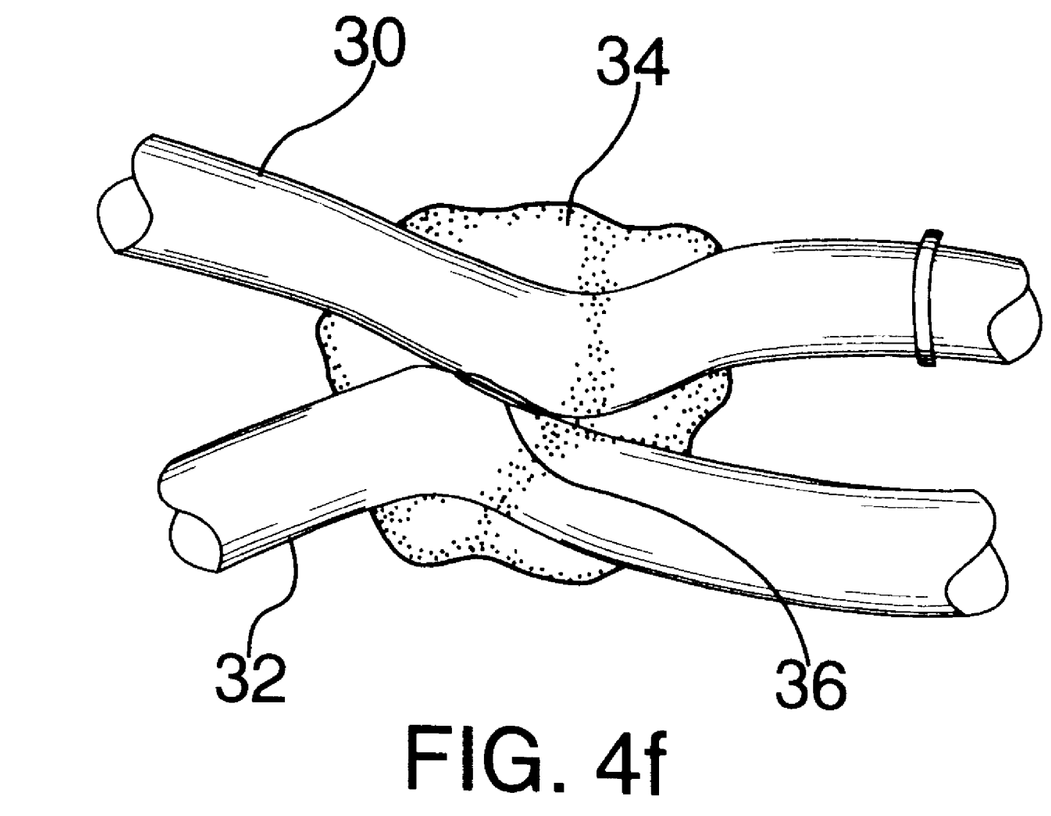

In a more preferred embodiment, a catheter device (FIG. 4) having a retractable needle 4, an extendable guide wire 6, an integral dilating device 8 and two expandable balloons 9 and 10 may be introduced into the lumen of the IMA 30 and fed up to the point of the desired arteriotomy. After positioning the IMA 30 in relation to the LAD 32, the needle 4 is extended and used to create an aperture both in the wall of the IMA 30 and the wall of the LAD 32 as shown in FIGS. 4(A)&(B). With the needle 4 in the LAD 32 the guide wire 6 is fed into the LAD 32 FIG. 4(B). The needle 4 is then retracted into the catheter device, leaving the guide wire 6 running from the IMA 30 through both arteriotomies into the LAD 32 as shown in FIG. 4(C). The catheter device is advanced along the guide wire 6 such that the integral dilating device 8 is pushed through both arteriotomy sites thereby dilating the arteriotomies. As used herein, the integral dilating device 8 comprises a tapered, generally conical, contour at the distal end of the catheter device. The integral dilating device having a proximal circumference substantially the same as the external diameter of the catheter device and a distal circumference smaller than the proximal circumference. The catheter device is inserted further into the LAD 32 until the distal balloon 9 lies within the LAD 32. The distal balloon 9 is then inflated, thereby stabilizing the distal balloon 9 within the LAD. The proximal balloon is then inflated thereby stabilizing the proximal balloon 10 within the IMA 30 and locking the IMA 30 and LAD 32 in place alongside one another as shown in FIG. 4(D). The bioadhesive 34 is then applied to seal the anastomosis site 36 as shown in FIG. 4(E). The catheter device is left in place until the bioadhesive 34 reaches sufficient strength to maintain the integrity of the anastomosis site 36, typically from about 30 seconds to about 5 minutes. The catheter device is then removed and the IMA 30 distal to the anastomosis site 36 clipped or ligated as shown in FIG. 4(F). The clamp proximal to the anastomosis is then removed from the IMA.

Alternatively, the dual balloon catheter includes balloons that can slide in relation to one another. In other words, one balloon slides toward or away from another balloon while that balloon remains in a fixed position. For example, the adjustable dual balloon catheter is introduced through the incised distal end of the IMA and is threaded proximally within the IMA through the IMA arteriotomy and into the LAD via the LAD arteriotomy. The proximal and distal balloons are then positioned just adjacent to the arteriotomy sites. After positioning the balloons, the distal balloon is inflated to a degree sufficient to stabilize it within the LAD. The proximal balloon is then inflated within the IMA. The distal balloon is then moved closer to, or slid toward, the proximal balloon thereby decreasing the distance between the balloons and the distance between the arteriotomies. Hence, the balloons are moved closer to one another until the proximal and distal balloons are located directly opposite one another just inside their respective arteriotomy sites. This sliding adjustment brings the arteriotomies into accurate alignment. If desired, the adjustable dual balloon catheter can have a locking mechanism that holds the two balloons in the chosen relationship. Locking the two balloons in position is especially helpful for the gluing procedure.

Figure 5A:
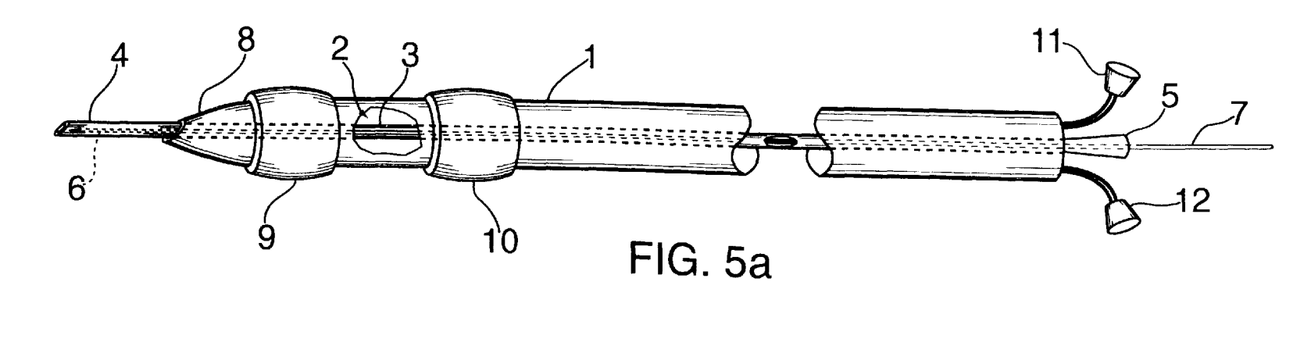
FIG. 5. illustrates two embodiments of a dual balloon catheter device.
Figure 5B:
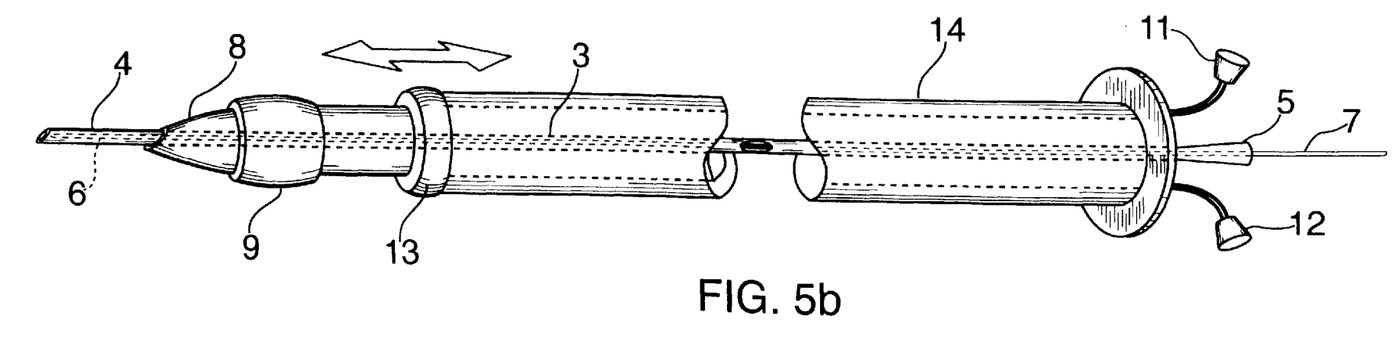

In an alternative embodiment, the adjustable catheter device has a retractable needle 4, an extendable guide wire 6, an integral dilating device, a distal expandable balloon and a proximal obturating device that is slidably related to the distal expandable balloon 9 as shown in FIG. 5B. As used herein, an obturating device, 13 or obturator, refers to an expanded annular portion of the catheter device having a diameter that is larger than the diameter of the catheter housing adjacent the expanded portion. The diameter of the obturating device is substantially similar to the diameter of the distal expandable balloon when inflated and is larger than the aperture created by the retractable needle. The obturating device may be integral to the catheter device, or it may be a separate, removable piece, like an "O-ring."

Another embodiment of the invention is directed to a catheter device for use in the method of the invention. This catheter device is a flexible tubular structure 1 that has at least one bore 2 running the length of the structure and is illustrated in FIG. 5. Preferably the device has one larger central bore and two smaller bores. Within the first tubular structure 1 is a second flexible tubular structure 3 that can slide within the first tubular structure and is located in the larger central bore 2. At the distal end of the second tubular structure 3 is attached a hollow, retractable needle 4. The second tubular structure 3, and its attached needle 4 has, at the end opposite the needle (the proximal end), a means 5 for holding the needle 4 in an extended position such that the needle can puncture an organ wall and a means for retracting the needle 4 so that the needle 4 can be pulled completely within the first tubular structure 1.

The second tubular structure 3 contains a guide wire 6 that runs at least the length of the device and that can slide within the second tubular structure 3 and the needle 4. At the proximal end of the guide wire 6 is a means 7 for extending the guide wire 6 through the distal end of the needle 4 and a means for maintaining the guide wire in an extended position when the needle is retracted. The first tubular structure 1 and the second tubular structure 3 can also slide together over the guide wire 6, and can be locked together if desired. The first tubular structure 1 is tapered at the distal end 8. Alternatively, a tapered dilating device can be attached to the distal end of the first tubular structure 1.

Proximal to the distal end of the first tubular structure is a first expandable balloon 9 and proximal to the first expandable balloon is a second expandable balloon 10. The first and second expandable balloons are attached to ports (11 and 12) or other means for inflating the balloons 9 and 10 using fluid or gas. Preferably, the first and second expandable balloons are positioned a sufficient distance apart to allow the walls of the structures to be apposed without crushing or damaging the walls between the inflated balloons. When the structures are blood vessels, the distance separating the two balloons is preferably about 1–2 mm. This distance will vary depending on the organs to be joined.

The size of the device according to the invention can vary depending on the organs being joined, but is preferably sized so that it can be used for endoscopic cardiac bypass surgery.

In another embodiment of the catheter device, the second expandable balloon 10 is attached to a sliding device 14. This sliding device 14 has a means for locking the expandable balloon into position such that the walls of the organs to be joined are held in apposition. Alternatively, the second expandable balloon is replaced by an obturator 13 larger than the arteriotomy produced by the needle with the obturator attached to a sliding device 14. For example, the obturator 13 is an integral part of the second tubular structure. Alternatively, the obturator 13 is a separate structure attached to the second tubular structure, such as the O-ring attached to the sliding mechanism illustrated in FIG. 5b. Thus, the obturating device 13 functions in the same way as the second expandable balloon 10 to hold the arteriotomy sites apposed to each other.

The invention is further described with reference to the following non-limiting examples.

EXAMPLE 1

Bioadhesive was mixed by extruding two solutions through an extruding device having a mixing tip; one solution contained 45% by weight bovine serum albumin and the second solution contained 10% by weight glutaraldehyde. The albumin and glutaraldehyde solutions were mixed in a 4:1 ratio by volume, albumin to glutaraldehyde. Harvested human saphenous veins were positioned adjacent to one another and secured. A small aperture was created in both veins by incising the vein wall, the aperture being the size needed to introduce an endarterectomy shunt through the aperture. One end of the shunt was fed into the lumen of one of the veins (vein 1), through the aperture in that vein and into the second vein (vein 2) via its aperture. The distal balloon, located within vein 1, was inflated and the vessels were manually pushed together, bringing the arteriotomies into direct apposition. The bioadhesive was mixed and applied, taking care to have the material completely surround the arteriotomies to provide a good seal. After the anastomosis was fully covered with adhesive, the adhesive was allowed to cure for two minutes and the shunt was removed.

The patency and integrity of the anastomosis was then tested. A syringe was attached by cannula to one of the veins. Fluid was passed through that cannula, demonstrating flow through that vessel. A clamp was placed at the end of the vessel opposite the syringe, more fluid was infused through the cannula, and fluid was observed coming from the second vein. The opening between the arteriotomies was thus proven to be patent. One end of the second vessel was clamped and a pressure gauge was attached to the other end. Fluid was then applied and a pressure of 370 mm Hg was achieved with no leaks evident at the anastomotic site. After leak testing, both vessels were opened opposite the anastomosis site, thereby exposing the anastomosis site. The anastomosis site was found to be clean with close vessel-to-vessel apposition and no frayed arteriotomy margins.

EXAMPLE 2

Bioadhesive was mixed by extruding two solutions through an extruding device having a mixing tip; one solution contained 4% by weight bovine serum albumin and the second solution contained 10% by weight glutaraldehyde. The albumin and glutaraldehyde solutions were mixed in a 4:1 ratio by volume, albumin to glutaraldehyde. A pig heart and a harvested human saphenous vein were positioned adjacent to one another and secured. An aperture was created in the vein and an arteriotomy was produced in the LAD of the heart; both the aperture and the arteriotomy were cut to the size necessary to introduce an endarterectomy shunt. One end of the shunt was fed into the lumen of the vein through the cut end of the vein and advanced through the aperture in the vein and into the LAD via the LAD arteriotomy. The distal balloon, located within the LAD, was inflated and the vein and the LAD were manually pushed together, thereby putting the aperture and the arteriotomy in direct apposition. The proximal balloon was then inflated. Bioadhesive was mixed and applied, taking care to have the material completely surround the anastomosis site to provide a good seal. After the anastomosis was fully covered with adhesive, the adhesive was allowed to cure for two minutes and the shunt was removed.

The patency and integrity of the anastomosis was then tested. A cannula was connected to the saphenous vein and a three-way valve attached to the cannula. To one port a syringe containing water was attached. To a second port in the three-way valve a pressure monitor was attached. The LAD was then clamped both proximal and distal to the anastomosis site and the saphenous vein was clamped at the end opposite the cannula. Water was then injected and the pressure was raised to 370 mm Hg with no leaking around the anastomosis site. After leak testing, both vessels were opened opposite the anastomosis site, thereby exposing the anastomosis site. The anastomosis site was found to be clean with close vessel-to-vessel apposition and no frayed arteriotomy margins.

The attachment of the saphenous vein to the LAD of the pig heart demonstrates, in vitro, the format of the beating heart coronary bypass procedure according to the invention in the absence of a beating heart.

An endarterectomy shunt has been used in a laboratory test of the invention. An endarterectomy shunt has two expandable balloons separated by a tubular section with a means for expanding both expandable balloons. However, an endarterectomy shunt cannot be used in a cardiac bypass procedure because it has a central bore that allows fluid to flow through the shunt and through both balloons; such a bore would allow blood to flow out of the artery to be anastomosed, thus causing hemorrhage. Hence, the endarterectomy shunt is useful to demonstrate the technique in the laboratory, but not useful under actual surgical conditions.

It is to be understood and expected that variations in the principles of construction herein disclosed in exemplary embodiments may be made by one skilled in the art and it is intended that such modifications, changes and substitutions are to be included with the scope of present invention.

We claim:

1. A device for joining a first hollow bodily organ to a second hollow bodily organ, comprising:
   (a) a first flexible elongated structure extending from a first proximal end to a first distal end, wherein a first longitudinal lumen extends within the first elongated structure from the first proximal end to the first distal end;
   (b) a distal annular inflatable balloon disposed around a distal portion of the first elongated structure;
   (c) a proximal annular inflatable balloon disposed around the first elongated structure proximal to the distal inflatable balloon;
   (d) a second flexible, elongated structure slidably received within the first longitudinal lumen, wherein the second elongated structure extends from a second proximal end to a second distal end, the second distal end forming a tissue piercing tip;
   wherein, the device, when in an operative position, is capable of having the distal balloon positioned within the second organ and the proximal balloon positioned within the first organ, and, when in a piercing position, the tissue piercing tip extends distally beyond the first distal end, and when in a retracted position, the tissue piercing tip is retracted within the first elongated structure.

2. The device of claim 1, further comprising:
   a third longitudinal lumen extending within the first elongated structure from the distal inflatable balloon to the first proximal end; and
   a fourth longitudinal lumen extending within the first elongated structure from the proximal inflatable balloon to the first proximal end.

3. The device of claim 1, further comprising:
   a second longitudinal lumen extending within the second elongated structure extending from the second proximal end to the distal end of the tissue piercing tip; and
   a guide wire slidably received within the second longitudinal lumen, the guide wire extending from a third proximal end to a third distal end;
   wherein, when in a guiding position, the third distal end is extended distally beyond the distal end of the piercing tip, and when in a non-guiding position, the third distal end does not extend beyond the distal end of the piercing tip.

4. The device of claim 1, wherein the piercing tip comprises a needle having a longitudinal lumen.

5. The device of claim 1, further comprising a piercing tip locking mechanism capable of reversibly locking the second elongated structure in at least one of the piercing position and the retracted position.

6. The device of claim 3, further comprising a guiding locking mechanism capable of reversibly locking the guide wire in at least one of the guiding position and the non-guiding position.

7. The device of claim 1, wherein the distance between the proximal inflatable balloon and the distal inflatable balloon is from about 1 to about 2 millimeters.

8. The device of claim 1, wherein the external diameter of the device is sufficiently small to allow use of the device through a surgical endoscope.

9. The device of claim 1, wherein the first distal end further comprises a tapered contour having a distal diameter that is smaller than a proximal diameter.

10. A device for joining a first hollow bodily organ to a second hollow bodily organ comprising:
   (a) a first flexible elongated structure extending from a first proximal end to a first distal end;
   (b) a proximal annular inflatable balloon disposed around a first distal portion of the first elongated structure;
   (c) a first longitudinal lumen extending within the first elongated structure from the first proximal end to the first distal end;
   (d) a second flexible elongated structure slidably received within the first longitudinal lumen, the second elongated structure extending from a second proximal end to a second distal end;
   (e) a distal annular inflatable balloon provided around a second distal portion of the second elongated structure;
   wherein, when the device is in an operative position, the distal balloon is received within the second organ, the proximal balloon is received within the first organ.

11. The device of claim 10, further comprising:
a second longitudinal lumen extending within the second elongated structure from the second proximal end to the second distal end; and
a third flexible elongated structure, slidably received within the second longitudinal lumen, wherein the third elongated structure extends from a third proximal end to a third distal end, the third distal end forming a tissue piercing tip;
wherein, when in a piercing position, the tissue piercing tip extends distally beyond the second distal end and when in a retracted position, the tissue piercing tip retracts within the second elongated structure.

12. The device of claim 11, further comprising:
a third longitudinal lumen extending within the third elongated structure from the third proximal end to the tissue piercing tip;
a guide wire slidably received within the third longitudinal lumen, the guide wire extending from a fourth proximal end to a fourth distal end;
wherein, when in a guiding position, the fourth distal end extends distally beyond the distal end of the piercing tip, and when in a non-guiding position, the fourth distal end does not extend beyond the distal end of the piercing tip.

13. The device of claim 10, further comprising:
a fourth longitudinal lumen extending within the first elongated structure from the proximal inflatable balloon to the first proximal end; and
a fifth longitudinal lumen extending within the second elongated structure from the distal inflatable balloon to the second proximal end.

14. The device of claim 10, wherein the proximal annular inflatable balloon is an obturator.

15. The device of claim 10, wherein the proximal annular inflatable balloon is replaced by an O-ring.

16. A method of anastomosing a first hollow bodily organ having a first aperture to a second hollow bodily organ having a second aperture, comprising the steps of:
A. inserting into the first hollow bodily organ a device comprising:
(a) a first flexible, elongated structure extending from a first proximal end to a first distal end, wherein a first longitudinal lumen extends within the first elongated structure from the first proximal end to the first distal end;
(b) a distal annular inflatable balloon disposed around a distal portion of the first elongated structure;
(c) a proximal annular inflatable balloon disposed around the first elongated structure proximal to the distal inflatable balloon;
B. apposing the first and second apertures to form an anastomosis site;
C. advancing the first elongated structure and the second elongated structure through the first aperture and second apertures into the second organ to a position wherein the distal inflatable balloon is received within the second organ and the proximal inflatable balloon is received within the first organ;
D. inflating the proximal and distal balloons to stabilize the first and second organs in an apposed position with the first and second apertures adjacent to one another; and
E. applying a bioadhesive to the anastomosis site thereby joining the first aperture to the second aperture.

17. A method of anastomosing a first hollow bodily organ to a second hollow bodily organ comprising the steps of:
A. inserting into the first hollow bodily organ a device comprising:
(a) a first flexible, elongated structure extending from a first proximal end to a first distal end, wherein a first longitudinal lumen extends within the first elongated structure from the first proximal end to the first distal end;
(b) a distal annular inflatable balloon disposed around a distal portion of the first elongated structure;
(c) a proximal annular inflatable balloon disposed around the first elongated structure proximal to the distal inflatable balloon;
(d) a second flexible, elongated structure slidably received within the first longitudinal lumen, wherein the second elongated structure extends from a second proximal end to a second distal end, the second distal end forming a tissue piercing tip;
wherein, when in a piercing position, the tissue piercing tip extends distally beyond the first distal end, and when in a retracted position, the tissue piercing tip retracts within the first elongated structure;
B. apposing a first wall of the first organ to a second wall of the second organ to form an anastomosis site;
C. extending the second elongated structure to the tissue piercing position;
D. piercing the first and second walls to form first and second apertures in the first and second walls respectively;
E. retracting the second elongated structure to the retracted position;
F. advancing the first elongated structure and the second elongated structure through the first aperture and second apertures into the second organ to a position wherein the distal inflatable balloon is received within the second organ and the proximal inflatable balloon is received within the first organ;
G. inflating the proximal and distal balloons to stabilize the first and second organs in an apposed position with the first and second apertures adjacent to one another; and
H. applying a bioadhesive to the anastomosis site to join the first aperture to the second aperture while maintaining fluid communication between the first organ and the second organ.

18. The method of claim 17, wherein the device further comprises:
a second longitudinal lumen extending within the second elongated structure extending from the second proximal end to the distal end of the tissue piercing tip; and
a guide wire slidably received within the second longitudinal lumen, the guide wire extending from a third proximal end to a third distal end;
wherein, when in a guiding position, the third distal end extends distally beyond the distal end of the piercing tip, and when in a non-guiding position, the third distal end does not extend beyond the distal end of the piercing tip.

19. The method of claim 18, wherein step F further comprises the step of:
extending the guide wire to the guiding position, wherein the third distal end is received within the second organ prior to advancing the first elongated structure and the second elongated structure through the first aperture and second apertures into the second organ to a position wherein the distal inflatable balloon is received within the second organ and the proximal inflatable balloon is received within the first organ.

20. The method of claim 19, further comprising the step of retracting the guide wire into the non-guiding position after inflating the distal inflatable balloon.

21. The method of claims 16 or 17, wherein the proximal and distal inflatable balloons are inflated with a fluid.

22. The method of claim 17, wherein the first and second hollow bodily organs are arteries.

23. The method of claim 17, wherein the first organ is the internal mammary artery and the second organ is the left anterior descending coronary artery.

24. A method of anastomosing a first hollow bodily organ having a first aperture to a second hollow bodily organ having a second aperture comprising the step of:
   A. inserting into the first hollow bodily organ a device comprising:
      (a) a first flexible elongated structure extending from a first proximal end to a first distal end;
      (b) a proximal annular inflatable balloon disposed around a first distal portion of the first elongated structure;
      (c) a first longitudinal lumen extending within the first elongated structure from the first proximal end to the first distal end;
      (d) a second flexible elongated structure slidably received within the first longitudinal lumen, the second elongated structure extending from a second proximal end to a second distal end;
      (e) a distal annular inflatable balloon provided around a second distal portion of the second elongated structure;
   B. apposing the first and second apertures to form an anastomosis site;
   C. extending the second elongated structure to the second position;
   D. advancing the second elongated structure through the first and second apertures into the second organ to a position wherein the distal inflatable balloon is received within the second organ;
   E. inflating the distal inflatable balloon, thereby stabilizing the distal balloon within the second organ;
   F. inflating the proximal inflatable balloon, thereby stabilizing the distal balloon within the first organ;
   G. retracting the second elongated structure into the first position, thereby apposing the first and second apertures between the proximal and distal inflatable balloons; and
   H. applying a bioadhesive to the anastomosis site to join the first aperture to the second aperture to provide fluid communication between the first organ and the second organ.

25. A method of anastomosing a first hollow bodily organ to a second hollow bodily organ, comprising the steps of:
   A. inserting into the first hollow bodily organ a device comprising:
      (a) a first flexible elongated structure extending from a first proximal end to a first distal end;
      (b) a proximal annular inflatable balloon disposed around a first distal portion of the first elongated structure;
      (c) a first longitudinal lumen extending within the first elongated structure from the first proximal end to the first distal end;
      (d) a second flexible elongated structure slidably received within the first longitudinal lumen, the second elongated structure extending from a second proximal end to a second distal end;
      (e) a distal annular inflatable balloon provided around a second distal portion of the second elongated structure;
      (f) a second longitudinal lumen extending within the second elongated structure from the second proximal end to the second distal end;
      (g) a third flexible elongated structure, slidably received within the second longitudinal lumen, wherein the third elongated structure extends from a third proximal end to a third distal end, the third distal end forming a tissue piercing tip;
      wherein, when in a piercing position, the tissue piercing tip extends distally beyond the second distal end and when in a retracted position, the tissue piercing tip retracts within the second elongated structure;
   B. apposing, at the site of anastomosis, a first wall of the first organ to a second wall of the second organ;
   C. extending the third elongated structure to the piercing position;
   D. piercing the first and second walls to form first and second apertures in the first and second walls respectively;
   E. retracting the third elongated structure to the retracted position;
   F. extending the second elongated structure to the second position;
   G. advancing the second elongated structure through the first and second apertures into the second organ to a position wherein the distal inflatable balloon is received within the second organ;
   H. inflating the distal inflatable balloon, thereby stabilizing the distal balloon within the second organ;
   I. inflating the proximal inflatable balloon, thereby stabilizing the distal balloon within the first organ;
   J. retracting the second elongated structure into the first position, thereby apposing the first and second apertures between the proximal and distal inflatable balloons; and
   K. applying a bioadhesive to the anastomosis site to join the first aperture to the second aperture to provide fluid communication between the first organ and the second organ.

26. The method of claim 25, wherein the device further comprises:
   a third longitudinal lumen extending within the third elongated structure from the third proximal end to the tissue piercing tip;
   a guide wire slidably received within the third longitudinal lumen, the guide wire extending from a fourth proximal end to a fourth distal end; wherein, when in a guiding position, the fourth distal end extends distally beyond the distal end of the piercing tip, and when in a non-guiding position, the fourth distal end does not extend beyond the distal end of the piercing tip.

27. The method of claim 26, wherein step G further comprises the step of:
   extending the guide wire to the guiding position, wherein the fourth distal end is received within the second organ prior to advancing the second elongated structure through the first and second apertures into the second organ to a position wherein the distal inflatable balloon is received within the second organ.

28. The method of claims 24 or 25, wherein the proximal inflatable balloon is an obturator.

29. The method of claim 26 wherein the first and second hollow bodily organs are arteries.

30. A method of performing a sutureless side-to-side anastomosis of two blood vessels comprising the steps of:
   A. isolating a first vessel;
   B. creating a first aperture in a wall of the first vessel;
   C. isolating a second vessel;
   D. creating a second aperture in a wall of the second vessel;
   E. positioning a multiple balloon catheter such that a first balloon is received within the first vessel and a second balloon is received within the second vessel;
   F. expanding the first and second balloons to stabilize said first and second apertures in apposition to form an anastomosis site; and
   G. applying bioadhesive to the anastomosis site to join the first and second apertures such that blood can flow between the first vessel and the second vessel.

31. The method of claim 30, wherein the first vessel is an internal mammary artery and the second vessel is a branch of the left coronary artery.

32. The method of claim 31, wherein between steps D and E, the method further comprises the steps of:

extending a guide wire from the first artery through the first and second apertures and into the second artery; and introducing the multiple balloon catheter through the first and second apertures along the guide wire.

33. The method of claim 30, wherein the distance between the first and second balloons can be slidably increased or decreased, and wherein the method further comprises the steps of:

expanding the first balloon in the first vessel;

expanding the second balloon within the second vessel; and sliding the first and second expanded balloons toward one another thereby bringing said apertures into direct apposition.

34. The method of claim 33, wherein the multiple balloon device comprises a lock mechanism adapted to lock the first and second balloons set distances from one another and wherein the method further comprises the step of locking the first and second balloons a set distance from one another before applying the bioadhesive.

* * * * *